United States Patent [19]

Nottke

[11] 4,427,006
[45] Jan. 24, 1984

[54] ELECTROSURGICAL INSTRUMENTS

[75] Inventor: James E. Nottke, Seminole, Fla.

[73] Assignee: Medical Research Associates, Ltd. #1, Clearwater, Fla.

[21] Appl. No.: 339,851

[22] Filed: Jan. 18, 1982

[51] Int. Cl.³ .............................................. A61B 17/39
[52] U.S. Cl. ........................... 128/303.14; 128/303.17; 200/159 B; 200/302.1
[58] Field of Search ....................... 128/303.13, 303.14, 128/303.17; 200/159 B, 302 A

[56] References Cited

U.S. PATENT DOCUMENTS

| 3,092,430 | 6/1963 | Miller | 339/32 |
|---|---|---|---|
| 3,648,001 | 3/1972 | Anderson et al. | 128/303.14 X |
| 3,799,168 | 3/1974 | Peters | 128/303.14 |
| 3,801,766 | 4/1974 | Morrison, Jr. | 128/303.14 |
| 3,807,404 | 4/1974 | Weissman | 128/303.14 |
| 4,021,630 | 5/1977 | Taylor | 200/159 B |
| 4,032,738 | 6/1977 | Esty et al. | 128/303.13 X |
| 4,034,761 | 7/1977 | Prater et al. | 128/303.14 |
| 4,112,950 | 9/1978 | Pike | 128/303.14 |
| 4,170,234 | 10/1979 | Graham | 128/303.14 |

FOREIGN PATENT DOCUMENTS 783141  4/1968  Canada .......................... 200/302 A

*Primary Examiner*—Lee S. Cohen
*Attorney, Agent, or Firm*—James R. Hulen

[57] ABSTRACT

An electrosurgical instrument for providing an interface between an electrosurgical electrode and an electrosurgical generator and for selectively providing electrical energy to the electrode for cutting, coagulation and the like, is provided. A hollow handle removably supports an electrode in one end and receives a three wire cable through an opening in its other end. The wires of the cable are supported and positioned on a substantially flat insert which has three flat-headed contact pins forced therein to penetrate the outer insulation of the wires and establish electrical contact with the wires. A conductor plate overlies the insert and is equipped with four conductor strips for contacting the electrode and the three contact pins, respectively. Switch buttons have stems that extend through apertures in the wall of the handle for selectively activating the conductor strips. Snap dome springs between the stems and the conductor strips provide tactile and audible sensations for the operator, and protuberances on the upper surfaces of the conductor strips prevent the domes from inverting while they apply sufficient force to the conductor strips. The proximal end of the cable is secured to a connector having a base and cover providing a housing for the three wires. Contact pins provide electrical communication between the wires and three spring contacts having generally rounded contact ends.

1 Claim, 7 Drawing Figures

U.S. Patent  Jan. 24, 1984  Sheet 2 of 2  4,427,006
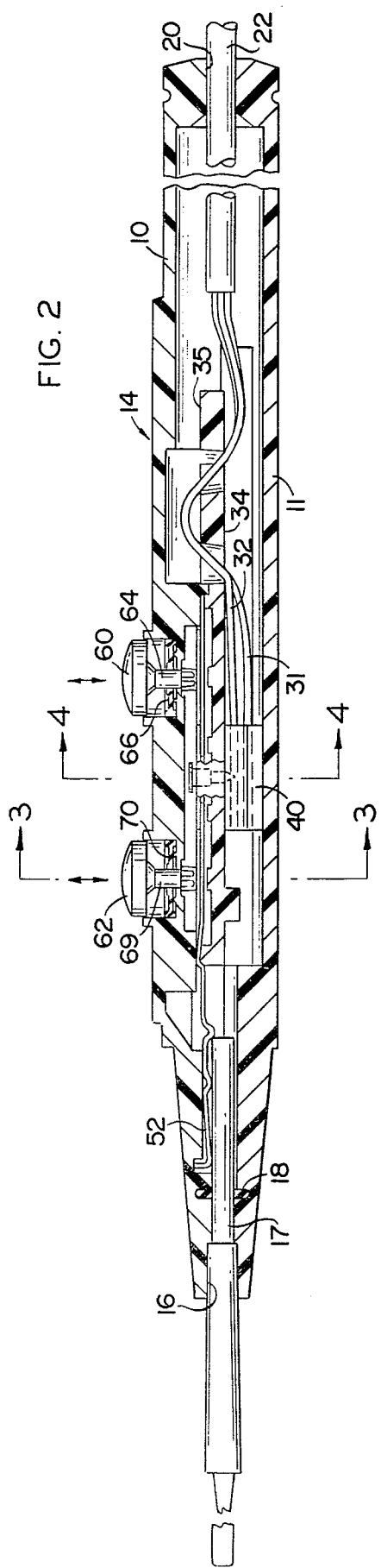
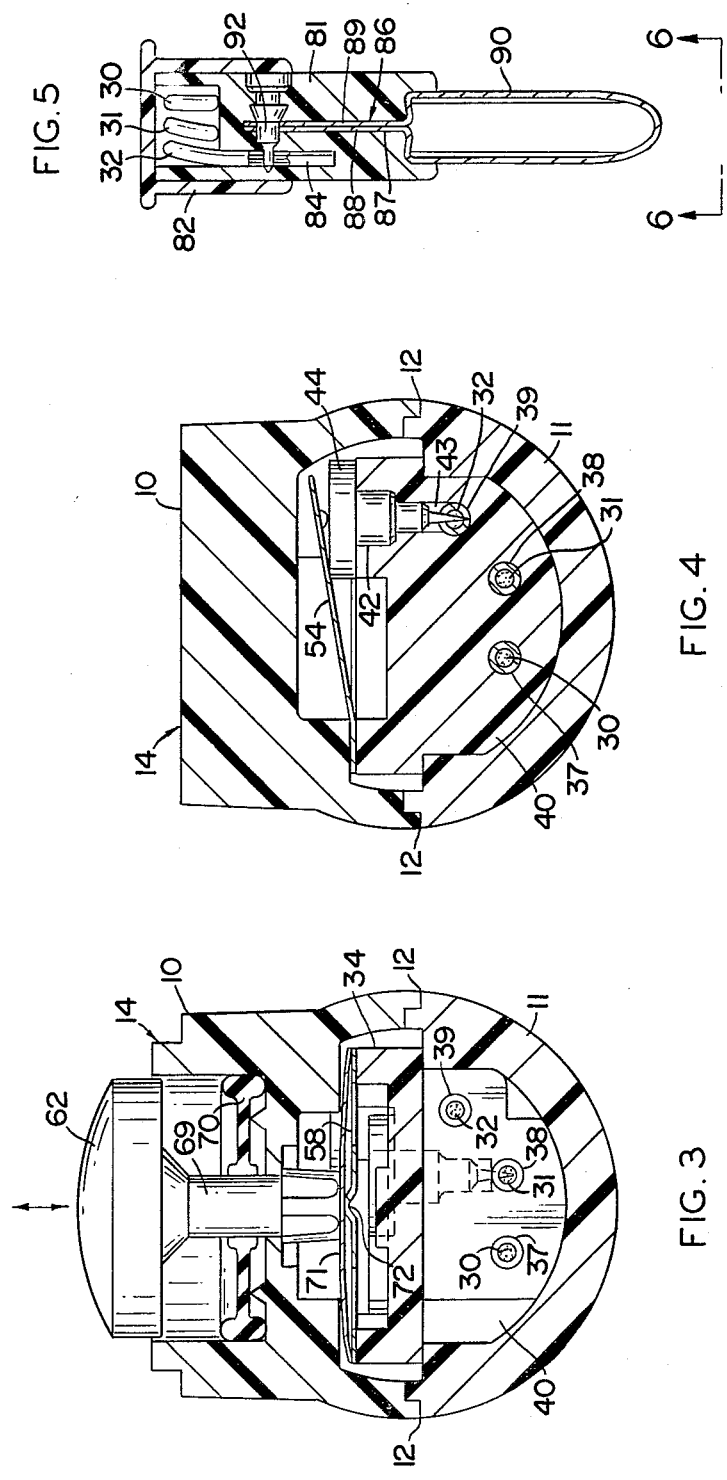
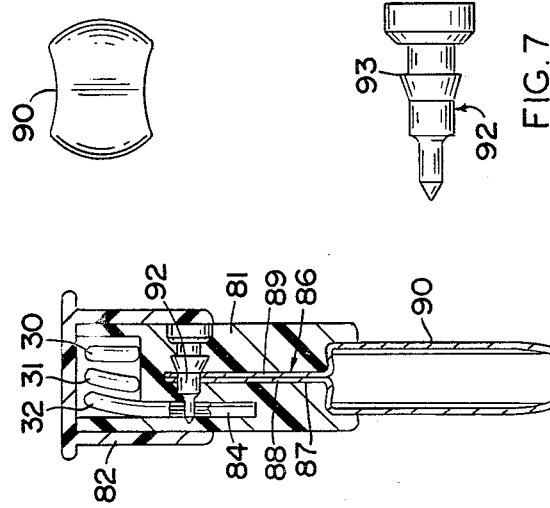
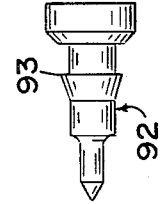
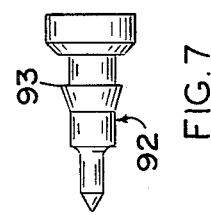
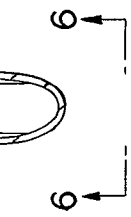

ELECTROSURGICAL INSTRUMENTS

BACKGROUND OF THE INVENTION

This invention relates to electrosurgical instruments and, more particularly, it is directed to improvements in the switching mechanism, generator connector and the general assembly of the instrument.

A field of medical instrumentation that has grown rapidly in recent years is electrosurgery, in which a suitable generator provides a high frequency, high voltage current which is transmitted to a small surgical electrode having an appropriate configuration for application to a patient. The patient normally is connected to a grounding plate or pad which is connected by a further conductor back to the generator. The relatively small area of contact by the electrode with the patient provides intense current in a highly localized area, producing a cutting action. The current passes through the patients body to the patient pad or plate where the area of contact is so great that no burning effect occurs.

For cutting purposes, the generator is activated to produce a continuous sine wave signal; however, the same instrument may be applied to the wound after cutting in order to produce coagulation. For this purpose the generator may be selectively activated to produce a pulsing signal which produces the desired results. A switching mechanism is available for the operator to selectively control an activating means for causing the generator to produce the desired type of current.

Although a number of arrangements have been devised for selectively activating the pulsing signal, the most satisfactory of these arrangements is a multiple wire cable conductor extending from the generator to the electrode holder. One conductor is normally connected to the electrode to carry the therapeutic current and two other conductors are selectively connectible to the therapeutic current conductor through switches to complete circuits back to the activating means for causing the generator to produce the desired mode of current. Previously available devices have provided mechanisms for supporting and positioning the wires of the multiple wire cable so that they could be connected to their respective electrodes or switches; however, the wire conductor support and positioning means have had many disadvantages in that the connections were expensive to achieve and failed to provide a positive connection. Furthermore, prior devices provided generator connectors at the proximal end of the multiple wire cable that created wear problems on the connector receptacles of the various generators with which the electrosurgical instrument was used. This condition was created primarily because of narrow lineal contact between the previous connectors and the connector receptacles of the generators.

SUMMARY OF THE INVENTION

The present invention provides an electrosurgical instrument construction that overcomes the difficulties mentioned above and provides a device that can be efficiently and inexpensively assembled.

The invention provides a unique mechanism for supporting and positioning a multiple wire cable conductor within a hollow elongated handle member which is adapted to receive a therapeutic electrode in its distal end. A uniquely designed conductor plate is utilized in combination with the wire support and positioning means which has a plurality of contact pins pressed into the surface thereof to securely position the wires and to provide a positive electrical connection with the conductive portion of the wires. This is accomplished by penetrating the insulation of the wires with sharp points on the contact pins.

The conductor plate provides positive electrical connection with an electrode that may be removably positioned within the distal end of the instrument. It also is equipped with cantilevered conductor strips that may contact the conductor pins which in turn have electrical communication with the wires. Switch buttons passing through appropriately aligned apertures in the hollow handle are adapted to depress two of the conductor strips for selective activation of the instrument. Snap dome springs may be located between the switch buttons and the conductor strips to transmit tactile and audible sensations to the operator and protuberances may be provided on the conductor strips to assist the operational function of the domes.

In addition to the unique mechanism for positioning and activating the wire conductors at the distal end of the multiple wire cable conductor, an improved generator connector is provided at the proximal end of the cable. The connector is provided with a unique means for securely positioning the ends of the wires in the connector and for achieving superior electrical communication between the wires and spring contacts that extend from the connector body. This connection is achieved by the use of uniquely designed contact pins which penetrate the insulation of the wires to establish electrical contact.

A further improvement of the present invention is the unique design of the spring contacts of the generator connector. Prior contact established essentially narrow linear contact with the connector receptable of the generator and thus created an undesirable wear problem. The present invention provides a spring contact that has a generally rounded configuration that facilitates insertion and removal of the contact and substantially reduces wear on the generator connector. A further advantage of the present invention is that it is watertight and, therefore, moisture can not penetrate the handle and create undesirable malfunction of the instrument.

BRIEF DESCRIPTION OF THE DRAWINGS

Various other advantages and features of novelty will become apparent as the description proceeds in conjunction with the accompanying drawings, in which:

FIG. 2 is a longitudinal cross sectional view of the electrosurgical instrument of the present invention;

FIG. 3 is a cross sectional view taken along line 3—3 of FIG. 2;

FIG. 4 is a cross section view taken along line 4—4 of FIG. 2;

FIG. 5 is a cross sectional view illustrating the generator connector of the present invention;

FIG. 6 is a view taken along line 6—6 of FIG. 5; and

FIG. 7 is an enlarged view of the contact pin utilized in FIG. 5.

DESCRIPTION OF PREFERRED EMBODIMENTS

Figure 1:
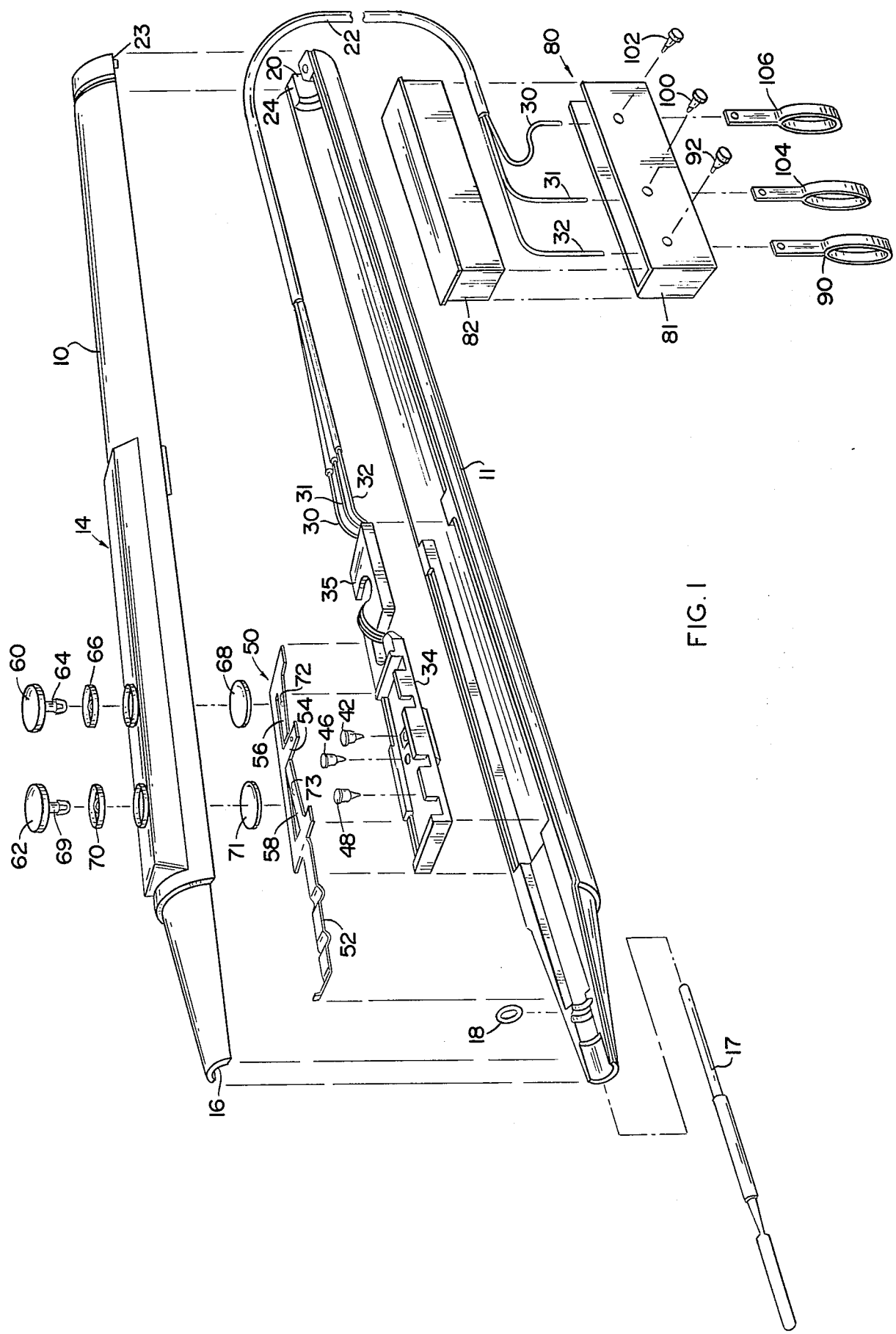
FIG. 1 is a perspective view illustrating the assembly of the various components of the present invention.

Referring to FIG. 1, a perspective exploded view of the disposable electrical instrument of the present invention is provided.

The electrosurgical instrument includes an elongated hollow handle which preferably is constructed from two halves or shells 10 and 11. Shells 10 and 11 coact along a longitudinal center line and preferably are molded from a thermoplastic resin, such as polystyrene or polypropylene, so that they may be ultrasonically welded together along line 12 to form the hollow handle 14 (see FIGS. 3 and 4).

Handle 14 has a first opening 16 at its distal end for receiving one end of a therapeutic electrode 17. Referring to FIG. 2, when electrode 17 is inserted into opening 16, it is firmly positioned therein and sealed against the entrance of moisture by an elastomeric ring 18 through which the proximal end of electrode 17 must pass. This structure, in combination with features to be described later in this application, provides a watertight compartment within handle 14 to eliminate hazards that may accompany the presence of moisture within the handle.

A second opening 20 is formed in the proximal end of handle 14 to receive and tightly secure multiple wire cable conductor 22. Inwardly directed flanges 23 and 24 on the proximal ends of shells 10 and 11, respectively, form opening 20 and are dimensioned to securely grip cable conductor 22 and thereby prevent the passage of moisture through the opening. If desired, additional sealing means (not shown) may be utilized in conjunction with flanges 23 and 24 to provide a more secure seal. These means may include additional inwardly directed flanges adjacent to flanges 23 and 24, or a more positive sealing means, such as an annular seal of foam or other suitable material.

Multiple wire cable conductor 22 preferably is provided with three conductor wires 30, 31 and 32. Wires 30, 31 and 32 are supported and positioned within handle 14 by an insert 34 which is seated within the handle and adapted to securely retain the ends of the wires. The secure connection and strain relief of the wires is accomplished by threading the wires through an "S" shaped portion 35 of insert 34 and then positioning the ends of the wires into passageways 37, 38 and 39 formed in a wire retaining block 40 extending downwardly from insert 34.

In order to provide therapeutic current to electrode 17, a unique switching mechanism is provided that will now be described in detail. To positively secure conductor wires 30, 31 and 32 within their respective passageways, contact pins having sharp points are forced into downwardly extending bores within insert 34 into contact with the wires. The points at the terminal ends of the contact pins penetrate the insulation of the conductor wires and establish electrical communication with the conductor portion of the wires. As shown in FIG. 4, contact pin 42 extends through a bore 43 formed in insert 34 and makes contact with conductor wire 32. Contact pin 42 has a relatively flat head 44 which is adapted to make contact with a conductor strip to be described below. Similar contact pins 46 and 48 (see FIG. 1) extend through bores in the upper surface of insert 34 to make electrical communication with their respective conductor wires 30 and 31.

Referring to FIG. 1, a conductor plate 50 overlies insert 34 and is provided with a plurality of cantilevered conductor strips 52, 54, 56 and 58. Conductor plate 50 preferably is made from a phosphor bronze material, but also may be made from nickel silver, stainless steel or other suitable spring-like conductive materials. Conductor strip 52 extends from the distal end of conductor plate 50 and is adapted to contact the end of electrode 17 when the electrode is positioned within the distal end of handle 14. A second conductor strip 54 extends laterally from conductor plate 50 in communication with head 44 of contact pin 42 to provide therapeutic current to electrode 17 (see FIG. 4). Conductor strip 52 and conductor strip 54 remain in contact with electrode 17 and contact pin 42, respectively, at all times. A third conductor strip 56 overlies contact pin 46 and a fourth conductor strip 58 overlies contact pin 48. Conductor strips 56 and 58 are selectively connectible to contact pins 46 and 48, respectively, to complete circuits back to the activating means for causing the generator to produce the desired mode of current.

The selection of current mode is achieved by the depression of either switch button 60 or switch button 62 which extend through the wall of handle 14 in communication with conductor strips 56 and 58 respectively. Switch button 60 is seated within an opening formed in the wall of handle 14 and has a depending stem 64 which passes through the opening into contact with conductor strip 56. An annular diaphragm seal 66 provides a secure seal around stem 64 and prevents the entry of moisture into hollow handle 14. In order to provide tactile and audible sensations for the operator, a snap dome spring 68 may be positioned between conductor strip 56 and the lower tip of stem 64. Similarly, stem 69, diaphragm seal 70 and snap dome spring 71 are provided in combination with switch button 62.

Because the snap dome springs perform a valuable function in the overall construction of the electrosurgical instrument of the present invention, it has been found to be desirable to provide a positive means to assure that the conductor strips will be effectively activated and that the springs will return to their upper positions when pressure is released on the switch buttons. To accomplish this, protuberances 72 and 73 are formed on the upper surfaces of conductor strips 56 and 58, respectfully. These protuberances are dimensioned to permit the snap dome springs, which are formed with convex upper surfaces and concave lower surfaces, to flex downwardly a sufficient distance to permit the tactile and audible sensations to occur, but not to completely reverse the curvature of the springs so that they cannot return to their original condition after pressure is released on the switch buttons. This is important because the snap domes could not transmit the proper force to the conductor strips without protuberances 72 and 73.

As previously stated, multiple wire cable conductor 22 passes through opening 20 in the proximal end of handle 14 and the conductor wires 30, 31 and 32 terminate in a generator connector 80 (see FIG. 1). Generator connector 80 is comprised of a base 81 into which the terminated wires are secured and a cover 82 for enclosing the wires within the base.

Conductor wires 30, 31 and 32 are securely positioned within base 81 in a manner similar to the distal ends of the wires. Referring to FIG. 5, wire 32 is shown positioned within a bore 84 located in base 81. A companion spring contact 86 is also secured within a bore 87 in base 81 and extends outwardly therefrom. Spring contact 86 is formed from a strip of electrically conductive material that is bent longitudinally upon itself to form two contiguous ends 88 and 89 which are connected by a generally elliptically shaped central portion 90. Ends 88 and 89 extend into bore 87 and are secured therein by a contact pin 92 which passes through one wall of base 81 through ends 88 and 89 into contact with the proximal end of conductor wire 32. Contact pin 92 is sharply pointed so that it penetrates the insulation of conductor wire 32 and thereby makes electrical contact with the wire. The detailed structure of contact pin 92 is illustrated in FIG. 7 in an enlarged view. It will be noted that the pin is equipped with outwardly extending annular flange 93 which facilitates the insertion of the pin into the wall of base 81 and cooperates with the plastic material of the base to securely position the pin within the base. Cover 82 is designed to extend over the heads of the contact pins and may be ultrasonically welded to the base to prevent accidental removal thereof.

Referring to FIG. 1, conductor wires 31 and 30 also are provided with contact pins 100 and 102 and spring contacts 104 and 106, respectively, for completing the structure of generator connector 80.

Spring contacts heretofore utilized with generator connectors have, because of the lineal contact between the wires and the generator receptacle, created a receptacle grooving problem. The spring contacts of the present invention, as illustrated in FIG. 6, have a lateral curvature in the generally elliptically shaped central portion to form a rounded contact end. This construction virtually eliminates the grooving problem experienced with prior devices.

The invention has been described in detail with particular reference to preferred embodiments thereof, but it will be understood that variations and modifications can be effected within the spirit and scope of the invention.

What is claimed is:

1. An electrosurgical instrument for providing an interface between an electrosurgical electrode and an electrosurgical generator and for selectively providing electrical energy to said electrode for cutting, coagulation and the like, comprising: an elongated hollow handle forming a housing having a first opening in its distal end for receiving said electrode and a second opening in its proximal end for receiving a cable; means in said first opening for forming a watertight seal when said electrode is inserted in said first opening; a cable having first, second and third wires extending through said second opening into said housing, said cable forming a watertight seal with inwardly directed flanges surrounding said second opening; insert means in said housing for supporting and positioning said wires; a contact pin in electrical communication with each of said wires; a conductor plate overlying said insert means, said plate having a first conductor strip positioned to contact said electrode, a second conductor strip contacting a first contact pin, a third conductor strip overlying a second contact pin and a fourth conductor strip overlying a third contact pin, said third and fourth strips being adapted to be depressed into contact with their respective contact pins; a first switch button mounted for communication with said third conductor strip through an aperture in said housing; a second switch button mounted for communication with said fourth conductor strip through a second aperture in said housing; snap dome springs mounted between said switch buttons and said third and fourth conductor strips for providing tactile and audible sensations when said switch buttons are depressed; protuberances formed on the surfaces of said third and fourth conductor strips under said snap dome springs for assuring activation of said strips and for preventing said springs from becoming inverted; and diaphragm seals around said switch buttons to prevent moisture from entering said housing thereby providing, in combination with the seals at said first and second openings, a watertight compartment within said housing.

* * * * *